(12) United States Patent
Hander

(10) Patent No.: US 8,513,306 B2
(45) Date of Patent: *Aug. 20, 2013

(54) ENHANCEMENT OF UROGENITAL FUNCTION

(76) Inventor: Robert W. Hander, Spokane Valley, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/978,312

(22) Filed: Dec. 23, 2010

(65) Prior Publication Data

US 2011/0166232 A1 Jul. 7, 2011

Related U.S. Application Data

(62) Division of application No. 11/617,601, filed on Dec. 28, 2006, now Pat. No. 7,858,599.

(60) Provisional application No. 60/743,086, filed on Dec. 30, 2005.

(51) Int. Cl.
*A01N 33/02* (2006.01)

(52) U.S. Cl.
USPC ......................................... 514/565

(58) Field of Classification Search
None
See application file for complete search history.

(56) References Cited

U.S. PATENT DOCUMENTS

| | | | |
|---|---|---|---|
| 4,057,644 A | 11/1977 | Pigerol et al. | |
| 5,767,159 A | 6/1998 | Hultman et al. | |
| 6,133,281 A | 10/2000 | Gonzalez-Cadavid et al. | |
| 6,479,069 B1 | 11/2002 | Hamilton | |
| 6,706,764 B2 | 3/2004 | Kaddurah-Daouk et al. | |
| 2003/0072822 A1 | 4/2003 | Ribnicky et al. | |
| 2003/0212136 A1 | 11/2003 | Vennerstrom et al. | |
| 2005/0124701 A1 | 6/2005 | Went et al. | |
| 2005/0267124 A1 | 12/2005 | Ziegler et al. | |

OTHER PUBLICATIONS

Silber M. Creatines: creatine and phosphocreatine as pharmacosanation aids. Sportscience—Encyclopedia of Sports Medicine & Science; available online, 1998. 557.
Albaha Baroawi, Eduard Gamito, Colin O'Donnell, and E. David Crawford, Hebei and Vitamin Supplement use in a Prostate cancer screening population. p. 288-292, 2004 Elsevier Inc.
Weisser et al., Enzyme activities in tissue of human benign prostatic hyperplasia after three months' treatment with the Sabal serrulata extract IDS 89 (Strogen®) or placebo. European Urology, 1997, vol. 31, No. 1, pp. 97-101.
Kato et al., The functional effect of mild outlet obstruction on the rabbit urinary bladder. J Urol. Oct. 1988;140(4):880-4.
Wilkinson, K. Artificial Urinary Sphincters Following Radical Prostatectomy. Nurse Times. Nov. 30-Dec. 6, 2004; 100 (48): 48-50 Airedale Primary Care Trust, Yorkshire.
Melvin H. Williams, Phd, and J. David Branch, PhD. Review Article; Creatine Supplementation and Exercise Performance; An Update. Review Article; journal of the American College of Nutrition, vol. 17, No. 3, 216-234 (1998).
Piotr Drabik, ; Creatine Stadion News International Sports Insider. The Newsletter for Winners. nners. vol. 8, No. 2, Spring. 2001. Island Pond, VT 05846, U.S.A.
Perlman, Susan L. MD; Symptomatic Disease-Modifying Therapy for the progressive Ataxias, Neurologist. 10(5): 275-289, Sep. 2004.

*Primary Examiner* — Daniel Sullivan
*Assistant Examiner* — Kyle Purdy
(74) *Attorney, Agent, or Firm* — Brian J. Pangrle

(57) ABSTRACT

A method of treating nocturia in a human individual includes administering dosages of creatine to the individual; and reducing the dosages of creatine to the individual responsive to an increase in difficulty of the individual to initiate urination. Another example method includes reducing the dosages of creatine to the individual responsive to an increase in nocturnal urination frequency of the individual. A dosing system includes doses of creatine for treating nocturia in a human individual and is configured for reduced doses for administration in response to an increase in one or more nocturia symptoms. Various other methods as well as compositions, systems, etc., are also disclosed.

7 Claims, 1 Drawing Sheet

ENHANCEMENT OF UROGENITAL FUNCTION

RELATED APPLICATIONS

This application is a divisional of U.S. Utility patent application having Ser. No. 11/617,601, entitled "Enhancement of Urogential Function", filed on Dec. 28, 2006 (U.S. Pat. No. 7,858,599, issue date of Dec. 28, 2010), which claims priority to U.S. Provisional Application Ser. No. 60/743,086, entitled "Enhancement of Urogential Function", filed Dec. 30, 2005, to Hander, the specification of the parent application and the provisional application are incorporated herein by reference.

TECHNICAL FIELD

The subject matter disclosed herein generally relates to dose delivery systems, compounds, compositions and methods for enhancing urogenital system function.

BACKGROUND

Local or systemic conditions can impair urogenital system function. Consider benign prostatic hyperplasia (BPH), which affects the walnut-sized prostate gland that surrounds the proximal urethra (the duct that drains the bladder). BPH commonly causes urinary tract symptoms secondary to bladder outlet obstruction. Bladder outlet obstruction has both a static component (structural and local) and a dynamic component (neurogenic and systemic). The static component is due to enlargement of the prostate gland, which commonly results in compression of the urethra and obstructed flow of urine from the bladder. The dynamic component is due to increased smooth muscle tone of the inner (involuntary) bladder neck sphincter. The dynamic component is at least partially regulated by alpha adrenergic sympathetic nervous system tone. Alpha adrenergic tone is mediated by way of alpha adrenergic synaptic receptors as well as by various second messenger pathways, including cyclic 3'-5' adenosine monophosphate (cAMP). Smooth muscle tone of the inner sphincter may also depend on extra-and intracellular $Ca^{2+}$ stores. Excessive inner sphincter smooth muscle tone results in bladder neck dysfunction.

Evaluation of BPH related urinary tract symptoms often includes use of an assessment test such as the International Prostate Symptom Score (I-PSS). A subject's I-PSS score is based on seven questions related to urination (incomplete emptying, frequency, intermittency, urgency, weak stream, straining, and nocturia). The nocturia question asks: "Over the past month, how many times did you most typically get up to urinate from the time you went to bed at night until the time you got up in the morning?" Patients with symptomatically significant BPH get up to urinate more times per night than is considered normal. Normal nocturnal urination frequency is zero or once. The symptom nocturia may also be considered to refer to difficulty initiating urine stream and complete bladder emptying during sleep hours.

Common treatments for BPH related urinary symptoms include administration of alpha adrenergic antagonists (alpha blockers) such as tamsulosin hydrochloride and terazosin hydrochloride. Alpha blockers decrease involuntary bladder sphincter tone of the prostatic urethra to promote free flow of urine and decreased urinary symptoms. Alpha blockers act on the dynamic component of bladder outlet obstruction. A common side effect of alpha blocker treatment is retrograde ejaculation.

Another common treatment for BPH related urinary symptoms acts on the static component of bladder outlet obstruction. It involves administration of the enzyme inhibitor finasteride. Finasteride is a competitive inhibitor of the enzyme 5areductase, which is responsible for the conversion of testosterone to dihydrotestosterone in the prostate gland. Dihydrotestosterone appears to be the major mitogen for prostate growth, and agents which inhibit 5a-reductase inhibit the progressive growth of the prostate which is characteristic of BPH. It thereby inhibits the progressive impairment of urine flow through the prostatic urethra with advancing age. Only men who already have significant prostate symptoms are likely to be treated with finasteride. Recognized side-effects of finasteride, experienced by around 6%-19% of users, include erectile dysfunction, and less often gynecomastia (breast gland enlargement).

The treatment of prostate symptoms as noted above are known to interfere with sexual functions such as penile erection and ejaculation. There are also physiologic interactions between the male reproductive and urinary systems. For example, it is normally not possible for males to voluntarily urinate while having an erection. Analogously it may be that nocturnal erections serve to prevent involuntary nocturnal bladder emptying. Both BPH and erectile dysfunction occur with increasing frequency over the age of fifty in men. It is not established whether there is a causal connection between these two common urogenital disorders of aging men. Various exemplary compounds, compositions and methods described herein aim to address urinary system and/or male reproductive system health and disorders. They may also address certain urinary system disorders in females.

DETAILED DESCRIPTION

Figure 1A:
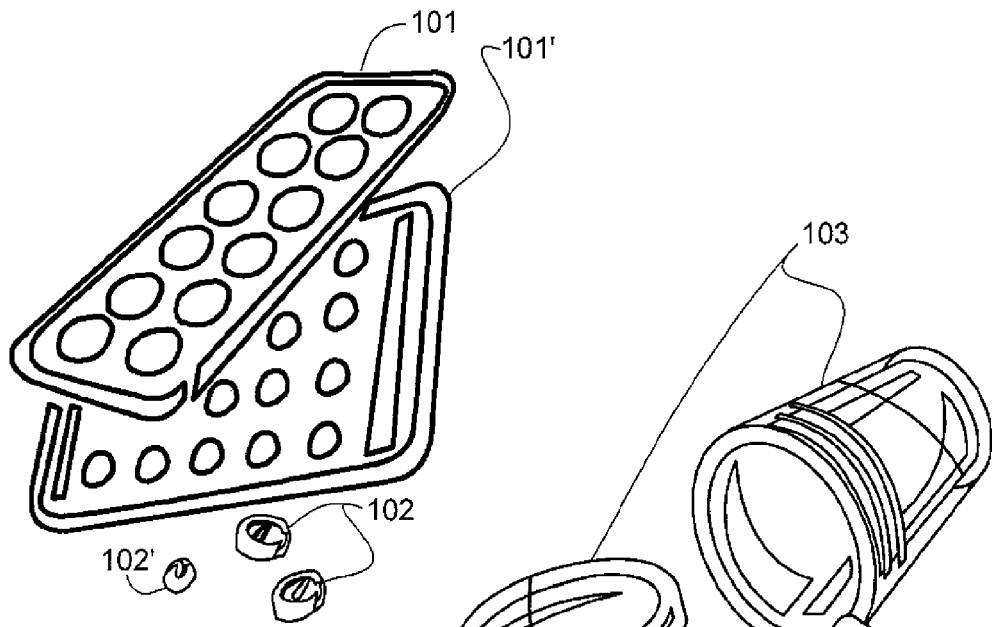
FIGS. 1A, 1B and 1C are arrangements for dose delivery.
Figure 1B:
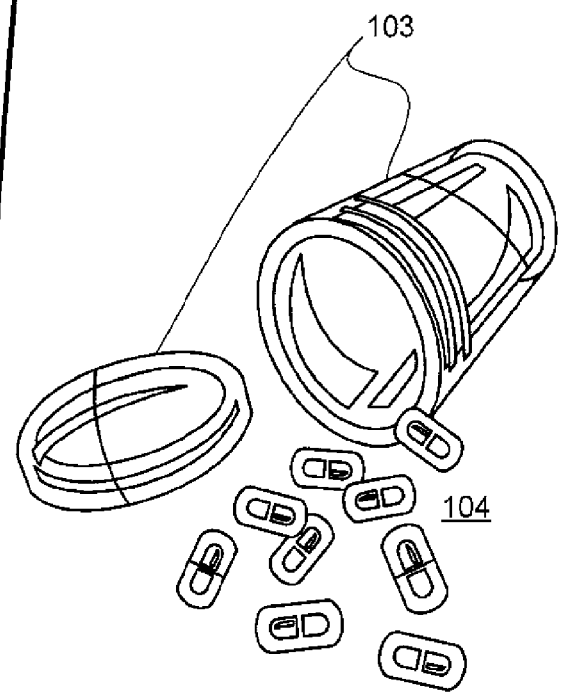
Figure 1C:
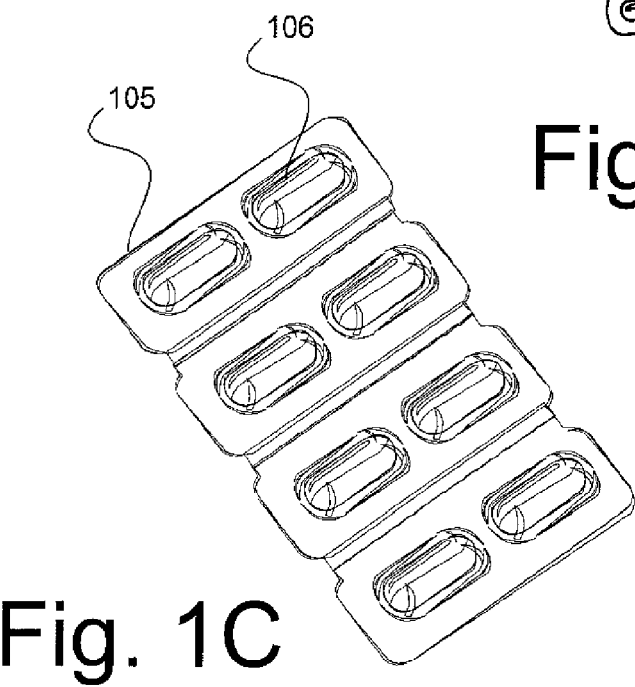

The following description includes the best mode presently contemplated for practicing various described implementations. This description is not to be taken in a limiting sense, but rather is made merely for the purpose of describing the general principles of the various implementations. The scope of the described implementations should be ascertained with reference to the issued claims. FIGS. 1A, 1B and 1C are referenced further below and illustrate dose delivery systems.

As mentioned in the Background section, prostate conditions such as BPH can alter normal urinary system functions and even reproductive system functions. In older men, a traditional association exists between BPH, prostatic urethral obstruction and urinary symptoms. As described herein, exemplary methods include administration of a compound or composition to alleviate or reduce urinary flow symptoms, especially for patients diagnosed with BPH. In addition, such methods can increase frequency of nocturnal erections, an indicator of normal reproductive system function. Consequently, various exemplary methods discussed herein can enhance quality of life by addressing urinary symptoms and sexual function.

An exemplary method includes ingestion of a compound that includes creatine. The preferred compound is phosphorylated creatine, which includes creatine monophosphate or phosphocreatine. Creatine is a nitrogenous amine. Normal daily dietary intake of creatine from an omnivorous diet approximates 1 g. Exogenous dietary sources of creatine include meat, fish, and other animal products, but it may also be formed endogenously in the liver, kidney, and pancreas from the amino acids glycine, arginine, and methionine. The normal daily requirement from either exogenous or endogenous sources approximates 2 g to replace catabolized creatine, which is excreted from the kidneys as creatinine.

Harris et al., "The concentration of creatine in meat, offal and commercial dog food", *Res Vet Sci.,* 1997 January-February; 62(1):58-62, reported concentrations of creatine (Cr), phosphorylcreatine (PCr) and creatinine (Cn) in a variety of meats, before and after cooking by boiling, in a range of commercially available canned dog foods, in rendered and dried meat products and in commercially available dry dog foods. Harris et al. noted that none of the samples contained PCr. They also reported that uncooked chicken, beef and rabbit meat contained approximately 30 mmol $kg^{-1}$ of Cr. Ox-heart and ox-liver had Or concentrations of 22.5 and 2.3 mmol $kg^{-1}$, respectively. Canned dog foods had Or concentrations of 0.5 to 2 mmol $kg^{-1}$. Dried meat samples had Or concentrations of 90 to 100 mmol kg–1 dry weight. In contrast, the Or concentration of dried rendered meat meal was 3 mmol $kg^{-1}$ dry weight or less. Dry dog foods contained 0.5 to 4 mmol $kg^{-1}$ dry weight of Cr. Harris et al., reported that their results indicate that in the canned dog foods, the dried meat samples and the dried rendered meat meal creatine had been degraded to variable extents to creatinine.

Based on the study of Harris et al., and the kinetics of phosphocreatine, it is expected that processed and cooked meats, poultry and fish supply very little phosphocreatine to an individual's diet.

Approximately 120 g of creatine is found in a 70 kg male, 95% in the skeletal muscle. Total creatine (TCr) exists in the muscle as both free creatine (FCr) and phosphocreatine (PCr). About 60% of the TCr is PCr, and the remainder is FCr. Creatine is an important source of chemical energy for muscle contraction because it can undergo phosphorylation that is both rapid, with the formation of PCr, and reversible, with donation of the phosphate group to adenosine diphosphate (ADP) to form adenosine triphosphate (ATP). This phosphorylationdephosphorylation reaction, catalyzed by the enzyme creatine kinase, is a rapid source of high-energy phosphate for performing high-intensity, short-duration physical activity.

Intramuscular supplies of both high-energy phosphagens ATP and PCr are limited, with the combined total being estimated to sustain very high-intensity exercise for approximately 10 seconds. Theoretically, creatine supplementation could increase [TCr], possibly facilitating the generation of intramuscular [PCr] and subsequent ATP formation, prolonging the duration of high-intensity physical activity.

A preferred exemplary compound is phosphorylated creatine. A common form of phosphorylated creatine is phosphocreatine, also known generally as creatine phosphate or creatine monophosphate and sometimes abbreviated PCr. Phosphorylate creatine is an important storage form of high energy phosphate, the energy source for muscle contraction. As described herein, the preferred exemplary compound is typically referred to as creatine monophosphate. Other forms of phosphorylated creatine may be used as an exemplary compound and appropriate CSUE doses determined, for example, using stoichiometry and/or comparisons to creatine monophosphate doses. Another creatine compound is creatine monohydrate. Yet another form of creatine is creatine ethyl ester, or simply creatine ester. Theories suggest that the ethyl ester allows for easy absorption in the intestines and that this form can be taken directly into a muscle cell through the cell wall.

Creatine (2-Amino-1,5-dihydro-1-methyl-4H-imidazol-4-one) has a molecular mass of about 131 g/mol. Creatine monohydrate has a molecular mass of about 149 g/mol. Creatine monophosphate, the preferred form of a phosphorylated creatine compound, has a molecular mass of about 210 g/mol. For purposes of comparison, 5 g of creatine monohydrate yields 4.40 g of creatine, 5 g of creatine monophosphate yields 3.12 g of creatine and 5 g of creatine citrate yields 2 g of creatine. Where a range or amount is referenced with respect to one form, conversion to another form is possible using such relationships or other relationships for yet other forms of creatine.

Creatine use is common among professional athletes and its use has spread to college athletes and recreational athletes that seek to enhance performance of high-intensity, short-duration exercise. Most creatine supplement regimens (CSRs) include a loading dose of 20 g to 30 g divided in 4 equal doses for 5 days to 7 days (e.g., approximately 0.3 g/kg/day), followed by a 2 g to 3 g per day maintenance dose. Levels of skeletal muscle creatine return to normal within about 2 weeks to 4 weeks after oral supplementation ceases.

As described herein, creatine monohydrate is useful at doses lower than 1.8 g per day. For a subject with a body weight of about 75 kg, a 2 g dose of creatine-monohydrate (about 1.8 g creatine) corresponds to approximately 27 milligrams (mg) creatine monohydrate per kg body weight (24 mg creatine). In an example described below, a subject with a body weight of about 78 kg ingested 88 mg per day of creatine to improve urologic condition, which corresponds to approximately 1.1 mg of creatine per kg body weight. Creatine supplementation for urologic enhancement is referred to herein as CSUE, hence, doses lower than 1.8 g per day of creatine or less than approximately 24 mg of creatine per kg body weight may be considered CSUE dose levels. Various exemplary CSUE ranges are mentioned below that are below 24 mg of creatine per kg body weight.

While many athletes use the CSR dose levels to enhance performance of high-intensity, short-duration exercise, conceivably, increased levels of PCr could reduce reliance on anaerobic glycolysis as a replenishment source of ATP, and possibly mitigate the formation of lactic acid and enhance performance in high-intensity, more prolonged exercise tasks approximating 30 to 150 seconds. However, some reports have linked creatine dosage levels used for enhanced athletic performance to weight gain, cramping, dehydration, diarrhea, and dizziness. Creatine may decrease renal function, but only two case reports of this effect have been published (see, e.g., a review article entitled "Creatine Supplementation and Exercise Performance: An Update" by Williams and Branch, *J Am College of Nutrition*, Vol. 17, No. 3, 216-234 (1998)).

The aforementioned review of Williams and Branch presents a table summarizing 31 studies on creatine monohydrate supplementation for enhancing short-term, high-intensity performance. The lowest daily dose, without prior loading, is 3 g per day. The authors of this low dose study did not observe ergogenic effect for varsity football and track athletes. This study suggests that the minimum dosage required for the benefits discussed herein to treat one or more urologic symptoms is less than the dosage required for observation of an ergogenic effect (e.g., for athletes in competition). Further, the desired benefits discussed herein are, in general, germane to an older population (e.g., older men having prostate-related symptoms, erectile dysfunction, or other urologic symptoms, etc.).

An exemplary method includes providing creatine monophosphate powder and administering a dose of the creatine monophosphate powder. Other forms of creatine monophosphate are discussed below (e.g., tablet form, etc.).

A trial provided creatine monohydrate as a powder (about 100% creatine monohydrate) and administered a single dose (approximately 0.1 to 0.2 g) of the creatine monohydrate powder in a solution (about 0.09 to 0.17 g creatine) approximately 0.5 to 3 hours prior to sleep. Urinary flow-related symptoms were reduced for the immediate sleep period and for sleep periods during the following 48 hours. Further, in this trial an increase in nocturnal erections was noted as well as an increase in testicular blood flow as evidenced by palpable scrotal content enlargement.

In the aforementioned trial, the male subject aged about 57, had a history nocturia in the presence of diagnosed moderate prostate enlargement. The subject weighed approximately 80 kg (about 175 lbs). Thus, the dosage was about 0.9 mg of creatine per kg of body weight. Range may vary by individual and prior consumption of a creatine compound. A general range for CSUE may be from about 0.4 mg creatine monohydrate to about 4.0 mg creatine monohydrate per kg body weight per day (e.g., about 32 mg to about 320 mg per day for a subject weighing about 80 kg). As already mentioned, the various trials used creatine monohydrate powder (about 100%) in solution. Thus, in terms of creatine content, the general range for CSUE may be from about 0.35 mg creatine per kg body weight per day (e.g., about 0.4*(3.124.4/5) mg) to about 3.5 mg creatine per kg body weight per day (e.g., 4.0*(3.124.4/5) mg). While dose may vary from patient to patient, the dose is typically less than the dose for CSR.

Additional trials administered doses of creatine monohydrate in solution in a range of approximately 0.1 g to approximately 1.0 g over a period of days (in a loading phase) to the aforementioned male subject and to another male subject of similar weight (~85 kg), aged 77. The older male subject (whose main urinary symptom was frequent urination during the day) was administered a loading phase dose of about 0.25 g (250 mg) of creatine monohydrate in solution every 24 hours. Both subjects found that, after a loading phase lasting several days, the CSUE dose sufficient to achieve the desired effects could be lowered to about 0.05 g (50 mg) to about 0.15 g (150 mg) of creatine monohydrate in solution every other day for the younger subject and to about 0.125 g (125 mg) of creatine monohydrate in solution every other day for the older subject. In both subjects, symptoms were relieved. The post-loading phase is referred to herein as a maintenance phase. The dose may vary during the maintenance phase; however, it is generally at least 50% less than the dose used in a loading phase. Both subjects noted that doses of greater than 1 g (1000 mg) of creatine monohydrate after the loading phase produced less urinary symptom reduction. The younger subject noted that doses larger than about 0.25 g (250 mg) of creatine monohydrate in the maintenance phase made initiation of his urine stream at night more difficult until 24 hours to 48 hours later at which time it improved that symptom as it did with lower doses.

In these trials, urinary flow-related symptoms were reduced. In general, for these trials, a CSUE dose at least an order of magnitude less than the maintenance dose typically used for athletic reasons (i.e., a CSR dose) reduced urinary flow-related symptoms. For example, a single dose less than approximately 0.17 g (170 mg) of creatine reduced urinary flow-related symptoms whereas a typically reported minimum maintenance athletic dose is 1.2 g (1200 mg) of creatine, which is about an order of magnitude higher. Further, the trials with the younger subject showed that such CSUE doses of creatine increased frequency and duration of nocturnal erections.

Trial results demonstrated that initial dose of a loading phase would relieve symptoms within 24 hours. However, in various trials, a delay in relief was experienced that corresponded to the dose size where a larger than required dose would actually delay relief (e.g. beyond 24 hours to as much as 72 hours). In other words, too small of a dose of creatine would not relieve symptoms, a range of doses of creatine would relieve symptoms within 24 hours and larger doses of creatine would cause a delay in the relief to beyond 24 hours. Such trials indicate that a dosage range exists for relief of symptoms and for timing of the relief.

An exemplary method includes administering loading phase doses of about 0.17 g (170 mg) to about 0.44 g (440 mg) of creatine per day to a male weighing about 80 kg for several days up to one month. According to such a method, if relief of symptoms does not occur within 24 hours of the initial loading phase dose, then the dose size may be reduced. Thereafter, administration of maintenance phase doses of about 0.44 g (44 mg) to about 0.22 g (220 mg) of creatine per day may occur. These doses are given as examples and may be differ depending on patient condition, while, in general, the maintenance doses of creatine are less than CSR doses.

ED and Creatine

According to various exemplary compounds, compositions and methods described herein, a link exists between nocturnal erectile function and urethral sphincter function. In general, an exemplary composition that includes creatine may be enhanced by including another compound that promotes nocturnal erections. Noting, that by itself, in an exemplary range of about 0.028 g (28 mg) to about 0.28 g (280 mg) of creatine per day for an adult male weighing around 80 kg, creatine can increase incidence of nocturnal erections.

Various pharmaceuticals are presently available to treat a condition generally known as erectile dysfunction (ED) or impotence. ED is a sexual dysfunction characterized by the inability to develop or maintain an erection of the penis for satisfactory sexual intercourse regardless of the capability of ejaculation. There are various underlying causes, such as diabetes, many of which are medically reversible. As noted above, the 5a-reductase inhibitor finasteride may cause ED as a side-effect.

A class of drugs known as phosphodiesterase type 5 inhibitors (PDE5 inhibitors) is used to treat ED. Prescription PDE5 inhibitors include sildenafil (VIAGRA®), vardenafil (LEVITRA®) and tadalafil (CIALIS®); these are normally taken orally. The mechanism operates through blocking the action of PDE5, which causes cyclic guanosine monophosphate (cGMP) to degrade. cGMP causes the smooth muscle of the arteries in the penis to relax, allowing the corpus cavernosum to fill with blood.

Sildenafil citrate has the formula $C_{22}H_{30}N_6O_4S.C_6H_8O_7$ and its IUPAC name is 1-[4-ethoxy-3-(6,7-dihydro-1-methyl-7-oxo-3-propyl-1H-pyrazolo[4,3-d]pyrimidin-5-yl) phenylsulfonyl]-4-methylpiperazine citrate (non-salt form about 474.6 g/mol).

Vardenafil has the formula $C_{23}H_{32}N_6O_4S$ and its IUPAC name is 4-[2-ethoxy-5-(4-ethylpiperazin-1-yl)sulfonyl-phenyl]-9-methyl-7-propyl-3,5,6,8-tetrazabicyclo[4.3.0]nona-3,7,9-trien-2-one (about 488.6 g/mol).

Tadalafil has the formula $C_{22}H_{19}N_3O_4$ and its official organic name is (6R,12aR)-6-(1,3-benzodioxo1-5-yl)-2,3,6,7,12,12a-hexahydro-2-methyl-pyrazino[1,2:1,6]pyrido[3,4-b]indole-1,4-dione (about 389.4 g/mol).

Part of the physiological process of penile erection involves the parasympathetic nervous system causing the release of nitric oxide (NO) in the corpus cavernosum of the penis. NO binds to the receptors of the enzyme guanylate cyclase which results in increased levels of cGMP, leading to smooth muscle relaxation (vasodilation) in the corpus cavernosum, resulting in increased inflow of blood and an erection.

Sildenafil is a potent and selective inhibitor of cGMP specific phosphodiesterase type 5 (PDE5) which is responsible for degradation of cGMP in the corpus cavernosum. The molecular structure of sildenafil is similar to that of cGMP and acts as a competitive binding agent of PDE5 in the corpus cavernosum, resulting in more cGMP and better erections. Without sexual stimulation, and therefore lack of activation of the NO/cGMP system, sildenafil should not cause an erection. Tadalafil and vardenafil operate by the same mechanism.

A typical dose range for sildenafil is 25 mg to 100 mg taken once per day between 30 minutes to 4 hours before sexual intercourse. It is usually recommended that a patient start with a dosage of sildenafil of 50 mg and then lower or raise the dosage as appropriate. Sildenafil is typically sold in three dosages: 25 mg, 50 mg, and 100 mg. Some patients may adjust dose by cutting the pills in half, for example, with a pill cutter.

Vardenafil is available in 2.5 mg, 5 mg, 10 mg, and 20 mg doses in round orange tablets. The normal starting dose is 10 mg (roughly equivalent to 50 mg of sildenafil). Vardenafil is recommended to be taken about 25 minutes to about 60 minutes prior to sexual activity, with a maximum dose frequency of once per day. With respect to tadalafil, a 20 mg dose is comparable to a 100 mg dose of sildenafil. Tadalafil tablets are yellow, film-coated, and almond-shaped, and are produced in 5 mg, 10 mg and 20 mg doses and at some doses it can have an extended effect (e.g., reported 36-hour effect).

As described herein, an exemplary method includes administration of creatine and administration of a PDE5 inhibitor. For example, prior to sexual intercourse, a subject may ingest (e.g., orally) 88 mg of creatine and an appropriate dose of a PDE5 inhibitor (e.g., 2.5 mg to 100 mg depending on circumstances and type of PDE5 inhibitor).

In a trial, the subject aged about 57 years old, ingested approximately 88 mg of creatine and about 6.25 mg to 12.5 mg of sildenafil citrate (VIAGRA®) simultaneously at a time prior to sexual intercourse (e.g., four hours or less prior to sexual intercourse). The subject noted an increase in the effectiveness of the sildenafil citrate at these lowered doses.

An exemplary composition includes creatine and sildenafil. Such a composition may be, for example, in the form of a pill, a liquid, a gel, a patch, a lozenge or a suppository. An exemplary pill includes creatine monophosphate and sildenafil citrate. Such a pill may include a creatine monophosphate (a phosphorylated creatine) to sildenafil citrate ratio in a range of approximately 1:10 to 10:1 (consider, e.g., a 1:10 ratio that administers 10 mg PCr to 100 mg sildenafil citrate and a 10:1 ratio that administers 250 mg PCr to 25 mg sildenafil citrate). This range of ratios isgiven as an example as other ranges are possible. Such ranges may be used for other delivery forms. As noted, tadalafil and vardenafil doses are about 5 times less than the dose for sildenafil. Thus, the example range of approximately 1:10 to 10:1 may be adjusted accordingly (e.g., up to 50:1 for tadalafil and vardenafil, etc.).

An exemplary method provides for reduction of dose size of a PDE5 inhibitor. Such a reduction in dose size may allow a patient to reduce a side effect or side effects associated with the PDE5 inhibitor. In particular, as administration of an exogenous source of creatine has been shown in trials to increase effectiveness of a PDE5 inhibitor, the dose of the PDE5 inhibitor may be reduced.

Importantly, occurrence of adverse drug reactions (ADRs) with PDE5 inhibitors appears to be dose related. Headache is a very common ADR, occurring in >10% of patients. Other common ADRs include: dizziness, flushing, dyspepsia, nasal congestion or rhinitis. Some have reported sildenafil associated ADRs such as priapism, severe hypotension, myocardial infarction, ventricular arrhythmias, sudden death, stroke and increased intraocular pressure. Some have reported ADRs from sildenafil as include sneezing, headache, flushing, dyspepsia, prolonged erections, palpitations and photophobia. Some have reported visual changes including blurring of vision. The most commonly reported ADRs of tadalafil include headache, indigestion, back pain, muscle aches, flushing, and stuffy or runny nose. Common vardenafil-specific ADRs include nausea while infrequent ADRs include: abdominal pain, back pain, photosensitivity, abnormal vision, eye pain, facial oedema, hypertension, palpitation, tachycardia, arthralgia, myalgia, rash, itch, priapism.

Thus, ingestion of creatine can allow for a reduction in PDE5 inhibitor dose and thereby reduce an ADR or ADRs. Such an exemplary method may also reduce cost per dose of PDE5 inhibitor. Dose reduction of a PDE5 inhibitor through administration of creatine may also reduce a drug interaction between the PDE5 inhibitor and one or more other drugs (e.g., drugs which inhibit or induce CYP3A4, including HIV protease inhibitors, ketoconazole, itraconazole, etc.).

A cGMP PDE5 inhibitors may be optionally selected from the following group:

3-ethyl-5-[2-(2-methoxyethoxy)-5-(4-methylpiperazin-1-yl-sulphonyl)pyridin-3-yl]-2-(pyridin-2-yl)methyl-2,6-dihydro-7H-pyrazolo[4,3-d]pyrimidin-7-one;

3-ethyl-5-[5-(4-ethylpiperazin-1-ylsulphonyl)-2)2-methoxyethoxy)pyridin-3-yl]-2-(pyridin-2-yl)methyl-2,6-dihydro-7H-pyrazolo[4,3-d]pyrimidin-7-one;

3-ethyl-5-[5-(4-ethyl-4-oxidopiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one;

5-[2-(2-methoxyethyoxy)-5-(4-methylpiperazin-1-ylsulphonyl)pyridin-3-yl]-3-n-propyl-2-(pyridin-2-yl)methyl-2,6-dihydro-7H-pyrazolo[4,3-d]pyrimidin-7-one;

545-(4-ethylpiperazin-1-ylsulphonyl)-2-(2-methoxyethoxy)pyridin-3-yl]-3-n-propyl-2-(pyridin-2-yl)methyl-2,6-dihydro-7H-pyrazolo[4,3-d]pyrimidin-7-one;

(+)-3-ethyl-5-[5-(4-ethylpiperazin-1-ylsulphonyl)-2-(2-methoxy-1(R)-methyl ethoxy)pyridin-3-yl]-2-methyl-2,6-dihydro-7-Hpyrazolo[4,3-d]pyrimidin-7-one;

3-ethyl-5-[5-(4-ethylpiperazin-1-ylsulphonyl)-2-(2-methoxy-1(R)-methylethoxy)pyridin-3-yl]-2-(6-methylpyridin-2-yl)methyl-2,6-dihydro-7H-pyrazolo[4,3-d]pyrimidin-7-one;

5-[2-ethoxy-5-(4-ethylpiperazin-1-ylsulphonyl)pyridin-3-yl]-3-ethyl-2-(6-methoxypyridin-2-yl)methyl-2,6-dihydro-7H-pyrazolo[4,3-d]pyrimidin-7-one;

542-i-butoxy-5-(4-ethylpiperazin-1-ylsulphonyl)pyridin-3-yl]-2,3-diethyl-2,6-dihydro-7H-pyrazolo[[4,3-d]pyrimidin-7-one; and 5-[2-ethoxy-5-(4-ethylpiperazin-1-ylsulphonyl)pyridin-3-yl]-3-ethyl-241-pyridin2-yl)ethyl]2,6-dihydro-7H-pyrazolo[4,3-d]pyrimidin-7-one or a pharmaceutically acceptable salts of one of such compounds. Other compounds may be used that elevate cGMP levels (e.g., other cGMP PDE inhibitors).

Adamantane Derivatives

Adamantane derivatives include amantadine, memantine and rimantadine. Such compounds may be used in combination with creatine and optionally a PDE5 inhibitor or other compound mentioned herein. Antiparkinsonian and neuroprotective agents amantadine and memantine inhibit responses to N-methyl-D-aspartic acid (NMDA).

Amantadine (1-aminoadamantane (IUPAC adamantan-1-amine, about 151.25 g/mol), sold as SYMMETREL®) is an antiviral drug that was approved by the Food and Drug Administration in 1976 for the treatment of Influenzavirus A in adults. The drug has also been demonstrated to help reduce symptoms of Parkinson's disease and drug-induced extrapyramidal syndromes. As an antiparkinsonic it can be used as monotherapy; or together with L-DOPA to treat L-DOPA-related motor fluctuations (i.e., shortening of L-DOPA duration of clinical effect, probably related to progressive neuronal loss) and L-DOPA-related dyskinesias (choreiform movements associated with long-term L-DOPA use, probably related to chronic pulsatile stimulation of dopamine receptors). Amantadine has been shown to relieve SSRI-induced anorgasmia in some people, though not in all people. There have been anecdotal reports that low-dose amantadine has been successfully used to treat ADHD. Amantadine is a derivate of adamantane, like a similar drug rimantadine.

While the mechanism of its antiparkinsonic effect is not fully understood, it appears to be responsible for releasing dopamine from the nerve endings of the brain cells, together with stimulation of norepinephrine response. Furthermore, it appears to be a weak NMDA antagonist and an anticholinergic.

A trial involving the younger subject (age about 57 years) involved occasional administration of about 100 mg of amantadine for flu prophylaxis. The subject noted that such administration correlated with reduction in nocturnal urinary symptoms.

An exemplary method includes treating urologic problems with amantadine. An exemplary method includes treating urologic problems with amantadine and creatine. An exemplary method includes treating erectile dysfunction with amantadine and a PDE5 inhibitor, and optionally creatine. In the aforementioned methods that include administration of creatine, the amount of creatine may be a CSUE dose level.

An exemplary composition includes creatine and amantadine (e.g., pill or other form). An exemplary composition includes amantadine and a PDE5 inhibitor (e.g., pill or other form). An exemplary composition includes creatine, amantadine and a PDE5 inhibitor (e.g., pill or other form). In the aforementioned compositions that include creatine, the amount of creatine may be a CSUE dose level.

In a trial, the younger subject (age about 57 years) ingested small amounts of amantadine along with about 88 mg of creatine. The small amounts of amantadine were measured by opening a capsule of amantadine and pouring out small amounts. Ten individual administrations used less than one 100 mg capsule of amantadine. Thus, the dose of amantadine was approximately 5 mg to approximately 10 mg. The subject did not note any easily discernable effects on now mild LUTS but did note easily discernible sexual effects.

The aforementioned younger subject found that if amantadine (about 5 mg to about 10 mg) and creatine (about 88 mg) were taken shortly before sexual activity in conjunction with small amounts of VIAGRA® (a quarter of a 50 mg tablet or about 12.5 mg) or LEVITRA® (a quarter of a 10 mg tab or about 2.5 mg) with excellent results as to erectile function. Normally such small doses of either of the PDE5 inhibitor ED drugs is somewhat marginally effective. The subject noted that all three substances (creatine, amantadine and PDE5 inhibitor) seem to work quickly and well together even less than 45 minutes before sexual activity.

The subject had been using VIAGRA®, LEVITRA® and CIALIS® ED drugs in low doses for most conjugal sexual activity for the past four years. The subject noted good results with or without creatine, but somewhat better with creatine and excellent with the combination of amantadine, creatine and an PDE5 inhibitor ED drug.

The subject took increasingly small doses of DHEA to enhance libido, but found that about 5 mg of amantadine had a similarly beneficial but distinct effect. The subject described the effect as not seeming to be an androgen mediated effect but rather a "neurogenic" effect that enhances the readiness for and enjoyment of orgasm without a direct effect on libido.

The subject noted that the effect of amantadine seems additive to that of the PDE5 inhibitor ED drugs. Further, the subject noted that creatine seems to have the effect that a lower dose of a PDE5 inhibitor ED drug works just as well. Such a result may be by way of an effect on NO production.

The subject noted a body weight that varied little from about 78 kg over the past twenty plus years. The subject noted no use of blood pressure or other prescribed medications on a regular basis.

Memantine is a class of Alzheimer's disease medications acting on the glutamatergic system. The IUPAC name is 1-amino-3,5-dimethyl-adamantane and the molecular weight is about 179 g/mol. A typically dose of memantine is in the range of about 5 mg to about 10 mg b.i.d. (twice a day), with a maximum dose of about 20 mg/day.

Memantine is marketed under the brands AXURA®, AKATINOL®, NAMENDA® and EBIXAO. Memantine acts as an uncompetetive antagonist at different neuronal nicotinic neuronal receptors (nAChRs) at potencies similar to the NMDA receptor (N-methyl d-aspartate). Memantine also acts as an uncompetitive antagonist at the $5HT_3$ receptor (a ligand-gated $Na^+$ and $K^+$ cation channel, resulting in a direct plasma membrane depolarization), with a potency similar to that for the NMDA receptor.

Memantine is generally well-tolerated. Common adverse drug reactions ($\geqq 1\%$ of patients) include: confusion, dizziness, drowsiness, headache, insomnia, agitation, and/or hallucinations. Less common adverse effects include: vomiting, anxiety, hypertonia, cystitis, and increased libido.

An exemplary method includes treating urologic problems with memantine. An exemplary method includes treating urologic problems with memantine and creatine. An exemplary method includes treating erectile dysfunction with memantine and a PDE5 inhibitor, and optionally creatine. An exemplary method may include treatment with memantine and amantadine, optionally with creatine and/or a PDE5 inhibitor. In the aforementioned methods that include administration of creatine, the amount of creatine may be a CSUE dose level.

An exemplary composition includes creatine and memantine (e.g., pill or other form). An exemplary composition includes memantine and a PDE5 inhibitor (e.g., pill or other form). An exemplary composition includes creatine, memantine and a PDE5 inhibitor (e.g., pill or other form). An exemplary composition includes creatine, memantine, amantadine and a PDE5 inhibitor (e.g., pill or other form). In the aforementioned compositions that include creatine, the amount of creatine may be a CSUE dose level.

Creatine and Reductase Inhibitors

Adverse drug reactions (ADRs) experienced with 5a-reductase inhibitors are generally dose-dependent. Common ADRs include impotence, decreased libido, decreased ejaculate volume. 5a-reductase inhibitors are a group of drugs with antiandrogenic activity, used in the treatment of benign prostatic hyperplasia and androgenic (or androgenetic) alopecia. These drugs decrease the levels of available 5a-reductase prior to testosterone binding with the enzyme, thus reducing levels of dihydrotestosterone that derives from such a bond. 5a-reductase inhibitors are clinically used in the treatment of conditions which are exacerbated by dihydrotestosterone. Specifically, these indications may include: mild-to-moderate benign prostatic hyperplasia and androgenic (or androgenetic) alopecia. Drugs include finasteride (PROSCAR® and PROPECIA®) and dutasteride (AVODART®).

The enzyme 5α-reductase is involved in the conversion of testosterone to the active form dihydrotestosterone by reducing the Δ4,5 double-bond. In benign prostatic hyperplasia, dihydrotestosterone acts as a potent cellular androgen and promotes prostate growth-inhibiting the enzyme reduces the excessive prostate growth. In alopecia, pattern-baldness is one of the effects of androgenic receptor activation. Reducing the levels of dihydrotestosterone thus reduces alopecia.

An exemplary method includes administration of creatine and a 5α-reductase inhibitor. Such a method may contribute to enhanced urogenital function by way of gradual reduction of BPH. An exemplary composition includes creatine and a 5α-reductase inhibitor. An exemplary method includes administration of creatine and a 5α-reductase inhibitor to reduce one or more ADRs. For example, as already noted, a known ADR of finasteride is ED. Thus, an exemplary method may administer creatine to reduce ED associated with finasteride. The amount of creatine in a method and/or a composition may be a CSUE dose level.

Creatine and ACE Inhibitors

ACE inhibitors, or inhibitors of Angiotensin-Converting Enzyme, are a group of pharmaceuticals that are used primarily in treatment of hypertension and congestive heart failure, in most cases as the drugs of first choice. Sulfhydrylcontaining ACE inhibitors include captopril (CAPOTEN®); dicarboxylate-containing ACE inhibitors include enalapril (VASOTEC®/RENITEC®), ramipril (ALTACE®/TRITACE®/RAMACE®), quinapril (ACCUPRIL®), perindopril (COVERSYL®), lisinopril (LISODURO/LOPRILO/PRINIVILO/ZESTRILO) and benazepril; and phosphonate-containing ACE inhibitors include fosinopril (MONOPRIL®).

An exemplary method includes administration of creatine and an ACE inhibitor. Such a method may gradually reduce urogenital vascular insufficiency by way of increased physiologic vascuar compliance, possibly as a result of increased NO production. An exemplary composition includes creatine and an ACE inhibitor. The amount of creatine may be a CSUE dose level.

Creatine and Angiotensin II Receptor Antagonists

ACE inhibitors share many common characteristics with another class of cardiovascular drugs called angiotensin II receptor antagonists, which are often used when patients are intolerant of the adverse effects produced by ACE inhibitors. ACE inhibitors do not completely prevent the formation of angiotensin II, as there are other conversion pathways, and so angiotensin II receptor antagonists may be useful because they act to prevent the action of angiotensin II at the AT1 receptor.

An exemplary method includes administration of creatine and an angiotensin II receptor antagonist. Such a method may gradually reduce urogenital vascular insufficiency by increasing physiologic vascular compliance, possibly as a result of increased NO production. An exemplary composition includes creatine and an angiotensin II receptor antagonist. The amount of creatine in a method and/or a composition may be a CSUE dose level.

Some Examples of Other Compounds

With respect to other compounds, a study by Bargawi et al., "Herbal and vitamin supplement use in a prostate cancer screening population" *Urology*, 2004 February; 63(2): 288-92, studied patients using multivitamins and/or herbal supplements. Such multi-vitamins and/or supplements are optionally used in conjunction with creatine.

In particular, the study of Bargawi et al. reported most participants as taking multivitamins, selenium, or herbal supplements. The use of herbal agents such as saw palmetto and Urtica dioica for the treatment of LUTS, and the use of selenium, vitamin E, and phytoestrogens to prevent and treat prostate cancer, has become more popular in recent years. Saw palmetto (Latin name Serenoa repens) is fast becoming the most commonly used herb for the treatment of BPH. As reported in the study of Bargawi et al., controlled clinical trials on saw palmetto suggested that saw palmetto improves urologic symptoms and flow measures and was associated with fewer side effects compared with finasteride. It has been hypothesized that the mechanism of action of saw palmetto may be due to suppression of prostatic dihydrotestosterone levels by the inhibition of the enzyme 5a-reductase (see, e.g., finasteride).

The second most commonly used herbal extract in benign prostatic hyperplasia (BPH) treatment is an extract of *Pygeum africanum*, an evergreen tree of the Rosaceae family indigenous to Africa. As reported in the study of Barqawi et al., controlled trials involving 1562 men who received *Pygeum africanum* for the treatment of BPH indicated that this treatment provided moderate improvement in the combined outcome of urologic symptoms and flow measures.

An exemplary composition includes creatine and saw palmetto. An exemplary method includes administering a composition that includes a creatine and saw palmetto. An exemplary method includes administering creatine and saw palmetto.

Another exemplary composition includes creatine and an extract of *Pygeum africanum*. An exemplary method includes administering such a composition. An exemplary method includes administering creatine and an an extract of *Pygeum africanum*.

An exemplary composition includes creatine, saw palmetto and an extract of *Pygeum africanum*. An exemplary method includes administering such a composition. An exemplary method includes administering creatine, saw palmetto and an extract of *Pygeum africanum*.

An exemplary composition includes creatine and an herb or herb extract. An exemplary method includes administering such a composition. An exemplary method includes administering creatine and an an herb or herb extract.

An exemplary composition includes creatine and an extract from an evergreen species. An exemplary method includes administering such a composition. An exemplary method includes administering creatine and an an extract from an evergreen species.

Other exemplary compositions may include lycopene. The younger subject observed that, on occasion for one day at a time, a lack of nocturnal urine stream slowing. Lycopene is present in tomato products while other foods of interest include certain beans and blue berries. An exemplary method includes administering such a composition. For example, a composition that includes creatine and lycopene may be administered to a subject to treat a urologic disorder. An exemplary method includes administering creatine and lyocpene to treat a urologic disorder.

Another exemplary composition includes dehydroepiandrosterone (DHEA), which is one of the hormones produced by the adrenal glands. After being secreted by the adrenal glands, it circulates in the bloodstream as DHEA-sulfate (DHEAS) and is converted as needed into other hormones. Supplementation with DHEA-S (a form of DHEA) has resulted in increased levels of testosterone and androstenedione, two steroid hormones.

The conversion of DHEA into testosterone may account for the fact that low blood levels of DHEA have been reported in some men with erectile dysfunction. The findings of a double-blind trial using 50 mg supplements of DHEA taken daily for six months suggests that DHEA may improve erectile function in some men.

An exemplary composition includes creatine and DHEA. For example, a daily dose for such an exemplary composition may include about OA-0.09 g of creatine and about 2 mg of DHEA.

According to various exemplary compounds, compositions and methods described herein, a link exists between nocturnal erectile function and urethral sphincter function. In general, an exemplary composition that includes creatine may be enhanced by including another compound that promotes nocturnal erections. Noting, that by itself, in an exemplary range of about 22 mg to about 0.44 g (440 mg) per day for an adult male weighing around 80 kg, creatine can increase incidence of nocturnal erections.

An exemplary method includes administration of DHEA in a range of about 0.5 mg to about 5 mg a day for a body weight of about 80 kg (about 0.006 mg/kg/day to about 0.06 mg/kg/day). Such a method is optionally combined with a method that administers creatine where creatine may be administered at a CSUE dose level.

The younger subject (age about age 57) ingested progressively smaller doses DHEA alone and in combination with creatine in CSUE doses to investigate possibly additive effects. Combination of 1 mg to 2 mg of DHEA had beneficial effects on urogenital function for one day but had negative effects on urinary symptoms thereafter despite lingering beneficial effects on sexual function up to 3 to 4 days. It is speculated that the low DHEA dose temporarily increases testicular production of testosterone whereas larger doses directly inhibit FSH production.

A possible concern about using DHEA to enhance urogenital function is that it may provide a substrate to increase endogenous androgen synthesis by prostatic tissue, thereby promoting BPH. Thus, where such a concern exists, then use of DHEA may be avoided or sufficiently reduced. Monitoring may be performed to assess such a concern.

An exemplary method to treat urinary flow-related symptoms includes increasing the number of nocturnal erections. As described herein, such an exemplary method may increase the number of nocturnal erections by any of a variety of means. For example, an increase in nocturnal erections may be achieved through use of creatine at CSUE dose levels.

Dosing

An exemplary container or dose delivery system includes tablets of creatine and optionally one or more other compounds (see, e.g., aforementioned compounds). For example, a container may contain tablets with about 100 mg creatine monohydrate per tablet. Such tablets are optionally shaped to provide for halving to about 50 mg. An exemplary method includes administering about 3 of the tablets per day during a loading phase and then about 1 tablet per day during a maintenance phase. The weight of an active(s) in a tablet may be selected according to one or more CSUE dose levels.

An exemplary container or dose delivery system includes tablets that include creatine monohydrate and DHEA. For example, a tablet may include about 100 mg creatine monohydrate and about 1.0 mg DHEA. An exemplary method includes administering about 3 of the tablets per day during a loading phase and then about 1 tablet per day during a maintenance phase.

An exemplary container or dose delivery system includes tablets that include creatine monohydrate and a PDE5 inhibitor. For example, a tablet may include about 100 mg creatine monohydrate and about 25 mg of sildenafil citrate. An exemplary method includes administering a tablet prior to sexual intercourse (e.g., about 4 hours prior to about 30 minutes prior to sexual intercourse).

An exemplary container or dose delivery system may be a bottle, a foil pack, or other conventional package. As already mentioned, for athletic purposes, creatine monohydrate is supplied conventionally as a powder in a bottle where dose size is greater than 2 g (CSR dose). As described herein, relief of certain urologic symptoms is dependent on dose size and dose size is less than 2 g (e.g., CSUE dose). Thus, the exemplary dose delivery systems that easily allow for adjustment of doses in a ratio of about 10:1 (e.g., 50 mg to 500 mg or 25 mg to 250 mg, etc.) have advantages over the conventional powder in a bottle package, especially where a loading phase is beneficial. Further, tablets may be shaped to facilitate dose size reduction. For example, a 100 mg tablet may be shaped to be easily broken into two 50 mg tablets.

FIGS. 1A, 1B and 1C show various arrangements for dose delivery. FIG. 1A shows a dose delivery system with two packages 101, 101' wherein the package 101 contains a dose 102 and the package 101' contains a dose 102' where the dose 102 is larger than the dose 102'. For example, the system of FIG. 1A may include a loading package 101 with a loading dose 102 and a maintenance package 101' with a maintenance dose 102'. Note that the doses 102, 102' may include indicia for halving.

In another example, the two packages 101, 101' of FIG. 1A may include different compounds and/or compositions. For example, the package 101 may include a dose 102 of creatine monohydrate (e.g., a CSUE dose) and the package 101' may include a dose 102' of a PDE5 inhibitor (e.g., sildenafil citrate, vardenafil, tadalafil). A subject may then select to take a dose 102 and a dose 102' simultaneously or at different times. A subject may select to take a dose 102 on a daily basis and a dose 102' prior to sexual activity (e.g., intercourse or other sexual activity). In general, where sexual intercourse is mentioned in this description, other sexual activity may substitute for intercourse.

In yet another example, more than two packages may be supplied in a single product package (e.g., a box). For example, a box may include a package for creatine, a package for amantadine and a package for a PDE5 inhibitor.

FIG. 1B shows a dose delivery system that includes a lidded container 103 and pills or tablets 104. The pills or tablets 104 may be gel, compressed powder, etc., and optionally include indicia or other mechanism to allow for division (e.g., halving). The pills or tablets 104 may include creatine monohydrate and optionally another compound (e.g., sildenafil citrate, amantadine, etc.).

FIG. 1C shows a dose delivery system sometimes referred to as a foil pack where a foil pack 105 includes individual doses 106. Such doses may be gel, compressed powder, etc., and optionally include indicia or other mechanism to allow for division (e.g., halving).

An exemplary kit may be a so-called blister pack. Blister packs are well known in the packaging industry and are widely used for the packaging of pharmaceutical unit dosage forms such as tablets, capsules, and the like. Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably, the strength of the sheet is such that the tablets or capsules can be removed from the blister pack by manually applying pressure on the recesses whereby an opening is formed in the sheet at the place of the recess. Tablet(s) or capsule(s) can then be removed via the opening.

It may be desirable to provide a memory aid on a kit, e.g., in the form of numbers next to the tablets or capsules whereby the numbers correspond with the days of the regimen during which the tablets or capsules so specified should be ingested. Another example of such a memory aid is a calendar printed on the card, e.g., as follows "First Week, Monday, Tuesday, ... etc ... Second Week, Monday, Tuesday, ... ", etc. Other variations of memory aids are possible. A "daily dose" can be a single tablet or capsule or several pills or capsules to be taken on a given day or at a given time prior to sexual activity. In some instances, one dose of a compound or composition may be of a less frequent basis than a dose of another compound or composition. For example, creatine monohydrate at a CSUE dose may be daily while a PDE5 inhibitor dose may be just prior to sexual activity. Also, a daily dose of the first compound may be one tablet or capsule while a daily dose of the second compound may be several tablets or capsules and vice versa. A memory aid may reflect one or more of such variations.

One or more other pharmaceutical components may also be optionally included as part of an exemplary compound and/or composition so long interference or adverse effects are avoided with intended treatment of a urologic disorder or disorders.

The following formulation examples are illustrative only and are not intended to be limiting. In the formulations which follow, "active ingredient" means a compound(s), as discussed herein (e.g., creatine monohydrate, PDE5 inhibitor, adamantane derivative, etc.). In the formulations 1, 2 and 3, the active ingredient may be increased beyond 100 mg, if so desired. For example, a PDE5 inhibitor dose may be about 50 mg and a creatine monohydrate dose about 100 mg, hence, the active ingredient may be about 150 mg for this example. Adjustments to the other ingredients may be made accordingly (e.g., using ratios or other calculations), if required.

Formulation 1: Gelatin Capsules
Hard gelatin capsules are prepared using the following ingredient quantity (mg/capsule):

| Active ingredient | 0.25-100 |
|---|---|
| Starch, NF | 0-650 |
| Starch flowable powder | 0-50 |
| Silicone fluid 350 centistokes | 0-15 |

Formulation 2: Tablets
A tablet formulation is prepared using the following ingredients quantity (mg/tablet) where the components are blended and compressed to form tablets:

| Active ingredient | 0.25-100 |
|---|---|
| Cellulose, microcrystalline | 200-650 |
| Silicon dioxide, fumed | 10-650 |
| Stearate acid | 5-15 |

Formulation 3: Tablets
Another tablet formulation is for tablets as follows where ingredient quantity is given as mg/tablet:

| Active ingredient | 0.25-100 |
|---|---|
| Starch | 45 |
| Cellulose, microcrystalline | 35 |
| Polyvinylpyrrolidone (as 10% sol'n H2O) | 4 |
| Sodium carboxymethyl cellulose | 4.5 |
| Magnesium stearate | 0.5 |
| Talc | 1 |

In this example, the active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

While powder and tablets have been discussed, other forms for creatine monohydrate or other compounds include, but are not limited to, unencapsulated gel and liquid forms. Other forms may be in the form of a patch (e.g., for transdermal delivery), a suppository, etc. In general, a pharmaceutically acceptable vehicle, diluent or carrier may be used.

Indexes

An exemplary method comprises administering a test to a patient and then prescribing an exemplary composition (e.g., creatine, amantadine and/or ED drug, etc.) based at least in part on the test. A test may assess lower urinary tract symptoms (LUTS), which are more generally urologic symptoms (noting that impotence, erectile dysfunction, etc., are also urologic symptoms). For assessment of lower urinary tract symptoms several instruments have been developed. Most tests describe frequency of symptoms as a first basic step toward understanding patient condition.

The Boyarsky Score is a questionnaire to assess lower urinary tract symptoms. The questionnaire is designed to be completed by the physician. The symptom scoring system evaluates the severity of nocturia, frequency, hesitancy, intermittency, terminal dribbling, urgency, reduction of the size and force of the stream, dysuria and incomplete voiding.

The Madsen-Iversen Score is another questionnaire, also designed for completion by the physician. The questionnaire assesses urinary stream, straining to void, hesitancy, intermittency, bladder emptying, stress incontinence or post void dribbling, urgency, frequency and nocturia. The importance of the patient's perception of the symptoms has been recognized and new instruments for assessing severity, frequency and quality of life of lower urinary tract symptoms have been designed. Health measurements or scales can be used to directly inquire about the impact of the symptoms or the distress they cause.

The International Prostate Symptom Score (IPSS) questionnaire is a validated instrument that measures the occurrence of seven symptoms from the lower urinary tract (incomplete emptying, frequency, urgency, nocturia, straining, weak stream, hesitancy). The IPSS questionnaire includes one separate question concerning the quality of life, graded on a scale from 0 to 6.

The American Urological Association (AUA) symptom index is a validated questionnaire and includes seven questions covering frequency, nocturia, weak urinary stream, hesitancy, intermittence, incomplete emptying and urgency and two questions on quality of life.

The ICSmaleSF questionnaire includes 11 questions on lower urinary tract symptoms (hesitancy, straining, decreased stream, intermittency, incomplete emptying, urgency, urge incontinence, stress incontinence, unpredictable incontinence, nocturia, post-void dribbling) and one question on quality of life.

The Danish Prostatic Symptom Score (DAN-PSS) measures the occurrence of 12 symptoms. Moreover, it evaluates the symptoms both quantitatively and qualitatively, using both a symptom score and a distress score. This instrument has a sensitivity of 92% and a specificity of 94%. The DAN-PSS questionnaire also measures the occurrence of dysuria, post micturition dribbling and urinary incontinence, as well as measuring activities of daily living, none of which are covered by the IPSS questionnaire. The DAN-PSS questionnaire is well understood by men 40 years or older and is reliable and valid for the same purposes as the IPSS questionnaire. The Spearman correlation coefficient between the prevalence as measured with DAN-PSS and IPSS was 0.75 and the correlation coefficient between total DANPSS score and total IPSS score was 0.70.

Some Exemplary Methods, Compounds, Compositions, etc.

Various exemplary methods, compounds, compositions, dosing techniques, etc., are discussed herein. An exemplary method includes administering a daily dose of creatine to an individual wherein the daily dose lies in a range from about 0.35 mg to about 3.5 mg per kilogram body weight. An exemplary dose delivery system includes individual doses of creatine wherein the individual doses comprise 88 mg or less of creatine and a container to contain the doses.

An exemplary method of treating a urologic symptom includes administering a daily dose of creatine to an individual wherein the daily dose lies in a range from about 0.35 mg to about 3.5 mg per kilogram body weight. Such a method may further include administering a dose of a compound that inhibits phosphodiesterase at a time prior to sexual activity (e.g., less than approximately 4 hours). In this variation, the compound that inhibits phosphodiesterase may optionally be one or more of the following sildenafil, vardenafil and tadalafil.

An exemplary method of treating a urologic symptom includes administering a daily dose of creatine and administering a dose of a compound that includes DHEA. In this example, the method may administer a daily dose of a compound that includes DHEA. The dose of DHEA may lie in a range from about 0.006 mg to about 0.06 mg per kilogram body weight.

An exemplary method of treating a urologic symptom includes administering a daily dose of creatine and administering a dose of a compound derived from adamantane. For example, the compound derived from adamantane may optionally be one or more of amantadine, memantine and rimantadine.

An exemplary method of treating impotence includes administering to a patient in need of such treatment an effective amount of creatine and a compound which elevates cGMP levels. In such an example, creatine and a compound which elevates cGMP levels may be each administered orally. In other examples, creatine and/or a compound which elevates cGMP levels may be administered other than orally. In the foregoing method, the cGMP elevator may be a cGMP PDE inhibitor. In the foregoing example, the cGMP elevator may be a prostaglandin.

An exemplary method of treating impotence includes administering to a patient in need of such treatment an effective amount of (1) creatine wherein the effective amount of creatine lies in a range from approximately 0.35 mg to approximately 3.5 mg per kilogram body weight of the patient and a compound which elevates cGMP levels. In such an example, creatine and a compound which elevates cGMP levels may be each administered orally. In other examples, creatine and/or a compound which elevates cGMP levels may be administered other than orally. In the foregoing method, the cGMP elevator may be a cGMP PDE inhibitor. In the foregoing example, the cGMP elevator may be a prostaglandin.

An exemplary method of treating impotence includes administering to a patient in need of such treatment an effective amount of creatine and a compound which elevates cGMP levels such as a cGMP PDE inhibitor selective for the cGMP PDE5 isoenzyme. In this example, the cGMP PDE5 inhibitor may be sildenafil or a pharmaceutically acceptable salt thereof (e.g., a citrate salt).

In various examples, compounds may be administered together in a composition. For example, any of the foregoing creatine and other compound(s) may be administered together in a composition. As an alternative, or in addition to, creatine and other compound(s) may be administered separately. For example, creatine may be administered daily and another compound administered prior to sexual intercourse (e.g., less than approximately 4 hours prior to sexual intercourse).

An exemplary method of treating impotence includes administering to a patient in need of such treatment an effective amount of creatine, a compound which elevates cGMP levels and a compound derived from adamantane. For example, the compound derived from adamantine may optionally be one or more of amantadine, memantine and rimantadine.

An exemplary composition includes creatine and a compound that inhibits phosphodiesterase. Such a composition may be a powder, a solid, a gel, a liquid, etc. An exemplary composition may include creatine together with and sildenafil, vardenafil and/or tadalafil.

An exemplary composition includes phosphorylated creatine, a compound that inhibits phosphodiesterase and a compound derived from adamantane. An exemplary composition may include creatine together with and sildenafil, vardenafil and/or tadalafil and a compound derived from adamantane.

What is claimed is:

1. A method of treating nocturia in a human individual comprising: diagnosing nocturia in the individual; and
   administering dosages of creatine to the individual
   in an amount sufficient to decrease the nocturnal urination frequency of the individual.

2. The method of claim 1 wherein the administering administers dosages of less than about 3.5 mg per kilogram human body weight.

3. The method of claim 1 wherein the dosages comprise daily dosages.

4. The method of claim 1 wherein the creatine comprises creatine monohydrate.

5. The method of claim 1 wherein the diagnosing comprises evaluating an assessment test for urinary tract symptoms.

6. The method of claim 1 wherein the diagnosing comprises evaluating one or more questions of the International Prostate Symptom Score (I-PSS) questionnaire.

7. The method of claim 1 further comprising reducing the dosages of creatine to the individual if nocturnal urination frequency does not decrease.

* * * * *